(12) United States Patent
Jen et al.

(10) Patent No.: US 6,342,704 B1
(45) Date of Patent: Jan. 29, 2002

(54) METHOD AND APPARATUS FOR DETECTING NITRIDE RESIDUE ON SEMICONDUCTOR WAFERS

(75) Inventors: Shu-Chun Jen, Taipei; Shin-Fang Tong, Yung-Kang, both of (TW)

(73) Assignee: Taiwan Semiconductor Manufacturing Company, Ltd, Hsin Chu (TW)

( * ) Notice: Subject to any disclaimer, the term of this patent is extended or adjusted under 35 U.S.C. 154(b) by 0 days.

(21) Appl. No.: 09/368,195

(22) Filed: Aug. 4, 1999

(51) Int. Cl.[7] ............................................... G01N 21/88
(52) U.S. Cl. .............................. 250/559.4; 250/559.46; 356/237.4
(58) Field of Search ....................... 250/559.29, 559.39, 250/559.4, 559.41, 559.44, 559.45, 559.46; 356/237.2, 237.5, 237.4, 402, 425, 446; 438/16, 710, 724

(56) References Cited

U.S. PATENT DOCUMENTS 5,392,113 A * 2/1995 Sayka et al. ............ 250/559.45
5,444,265 A * 8/1995 Hamilton ................ 250/559.42

* cited by examiner

*Primary Examiner*—Kevin Pyo
(74) *Attorney, Agent, or Firm*—Tung & Associates

(57) ABSTRACT

Residue such as nitride remaining on the surface of a semiconductor wafer following plasma etching using nitride is detected after the wafer is transferred from the etching chamber to an exit load lock station. A pair of color sensors are coupled with a color analyzer to operate in a differential manner to analyze the color of the surface of the wafer. The presence of nitride residue is sensed as the color purple.

10 Claims, 2 Drawing Sheets

BEFORE NITRIDE ETCHING

NITRIDE RESIDUE

ETCHING OK

METHOD AND APPARATUS FOR DETECTING NITRIDE RESIDUE ON SEMICONDUCTOR WAFERS

TECHNICAL FIELD

The present invention broadly relates to semiconductor manufacturing operations, and deals more particularly with a method and apparatus for detecting the presence of etchant residue, and especially nitride residue on semiconductor wafers following an etching operation.

BACKGROUND OF THE INVENTION

An important process in the fabrication of integrated circuits is the removal of various layers of materials formed on a silicon wafer. Two major etching techniques are in common usage. One of these techniques is referred to as wet or chemical etching, wherein a photoresist patterned silicon wafer is immersed in a chemical solution. The other of such techniques is referred to as a dry or plasma etching, wherein a wafer is exposed to a plasma containing a gas.

Plasma etch processes and apparatus are generally well known for etching materials for semiconductor device fabrication. The process begins with application of a masking material, such as photoresist, to a silicon wafer. The masking pattern protects areas of the wafer from the etch process. The wafer is then placed in a plasma reactor or "etcher" and it is then etched. Subsequent steps are determined by the type of device being fabricated. This process is especially valuable for the definition of small geometries.

Plasma etching is basically anisotropic and eliminates undesirable under cutting. In this method, a gas such as $CF_4$ is injected into the chamber which contains the wafer to be etched. The chamber is maintained at a relative vacuum and the gas is converted into a plasma by the coupling of the chamber to an R.F. frequency power source. This creates radicals which are chemically reactive with the surface to be etched, thus removing the desired material which is continually removed from the chamber. Like all methods, it is important to detect when the desired overlying material has been completely removed. The sensing of the complete etching of a layer of material has been carried out in the past using any of several techniques. One such technique involves monitoring the plasma emission during etching, at a particular wavelength, and the intensity at that wavelength is then correlated to the remaining thickness of a film being etched. In this manner, it can be determined when one or more known film thicknesses remain over a substrate. Another technique involves spectroscopic monitoring of the substrate to determine when the atomic lines of certain elements, such as phosphorus disappear, as in the case of etching phosphorus-doped silicon dioxide. Still another technique for monitoring etch depth relies on the transparency to a visible light and a light having a wave length from about 400 nm to about 700 nm of substrate layers. Such a layer is transparent to incident visible light if it transmits at least 5% of the incident visible light. In this technique, visible light from, for example, a laser, is directed onto an uncovered area of the transparent layer undergoing etching, and the intensity of the light reflected from the layer is detected and recorded as a junction of time. Because the layer is transparent, the incident light is both reflected from the upper surface of the transparent layer and is transmitted through the layer. As etching proceeds, the thickness of, and thus the optical path length through the substrate layer being etched is reduced. Consequently, as specific thickness, destructive or constructive interference, which correspond to, respectively, a relative minimum and a relative maximum in the recorded density-time curve, occurs. It is possible to relate the time intervals between these intensity extremes to changes in etch depth.

In addition to the problem of monitoring etch depth, to assure that layers are completely etched to the desired level, it is also necessary to monitor wafers following etching to determine whether any contaminants remain on the wafer following the etching process. For example, one type of plasma etching relies on the use of a nitride to perform the etching task. This process, sometimes referred to as nitride etching, may, in some cases result in nitride residue to remaining on the surface of a wafer that causes nitride etching non-uniformity. This nitride residue represents a contaminant which has a damaging affect on the wafer when the wafer is subjected to subsequent processing steps. In the past, there has been no efficient means to detect the presence of nitride residue in the wafers after they exit the plasma chamber, before being transported to a subsequent processing station. As a result, the presence of undetected nitride residue on semiconductor wafers has caused the production of defective product, which in tun reduces yield and productivity.

Accordingly, their is a clear need in the art for a method and apparatus for detecting the presence of a nitride residue on the surface of a wafer immediately after it has been removed from the etching chamber.

SUMMARY OF THE INVENTION

According to one aspect of the invention, a method is provided for detecting the presence of nitride residue on the surface of a semiconductor wafer after a layer of material on a wafer has been etched using a plasma etching technique. The method includes the steps of subjecting the wafer surface to light; measuring the magnitude of light reflected from the wafer surface, having a wavelength within a range of wavelengths characterizing the color of the nitride residue; and comparing the measured magnitude with a reference value, the result of such comparison indicating the presence or absence of nitride residue on the wafer surface. In the case of a nitride etchant, the wavelength range of light is characteristic of the color purple. The light is preferably directed on to the surface of the wafer using a pair of color analyzers which also sense the light reflected from the wafer and analyzes its wavelength.

According to another aspect of the invention, a method is provided for etching a layer of material on the surface of a semiconductor wafer, which includes the steps of; transferring the wafer into a processing chamber; plasma etching a layer on the wafer using an etchant including a nitride; transferring the wafer out of the chamber after etching is complete; directing light onto the surface of the wafer after the wafer has been transferred out of the chamber; and measuring the light reflected from the wafer surface having a wavelength within a range of wavelengths that characterize nitride residue remaining on the wafer surface.

According to a further aspect of the invention, apparatus is provided for detecting the presence of nitride residue present on the surface of a semiconductor wafer, after the wafer has been removed from a chamber in which the wafer is etched. The apparatus includes a color differential sensor system for sensing and analyzing light reflected from the fully etched areas of the wafer surface and from areas containing the residue, the sensed differential indicating the presence or absence of the residue. The color differential sensor preferably includes first and second color sensors mounted so as to sense the color of light reflected from diametrically opposite sides of the wafer surface. The apparatus also includes means responsive to the sensor system for controlling the transfer of the wafer.

Accordingly, it is a primary object of the present invention to provide a method and apparatus for sensing the presence of a nitride residue on the surface semiconductor wafer after the wafer has been plasma etched.

A further object of the invention is to provide a method and apparatus as described above which detects the presence of nitride residue on the wafer surface immediately after the wafer exits an etch chamber, and before the wafer is transferred to a subsequent processing station.

Another object of the invention is to provide a method and apparatus as aforementioned which materially reduces scrap and increases yield by eliminating damaging contaminants on the wafer surface.

A further object of the present invention is to provide a method and apparatus of the type mentioned above which automates the process of inspecting wafers for nitride residue, thus increasing efficiency and reducing the possibility of inspection error.

These, and further objects and advantages of the present invention will be made clear or will become apparent during the course of the following description of the preferred embodiment of the invention.

BRIEF DESCRIPTION OF THE DRAWINGS

In the drawings, which form an integral part of the specifications and claims, and are to be read in conjunction therewith, and wherein like reference numerals are employed to designate identical components in the various views:

DETAILED DESCRIPTION OF THE PREFERRED EMBODIMENT

Figure 1A:
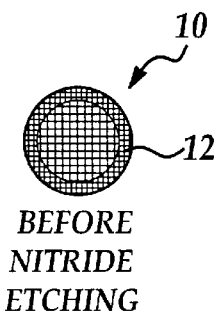
FIG. 1A is a plan view of a semiconductor wafer prior to nitride etching.
Figure 1B:
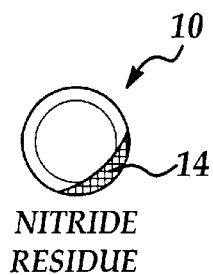
FIG. 1B is a view similar to FIG. 1A, but following the nitride etching step and showing nitride residue present on a wafer.
Figure 1C:
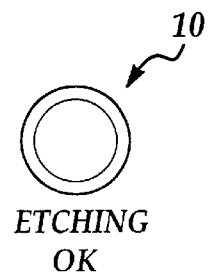
FIG. 1C is a view similar to FIG. 1A but showing the wafer fully etched without any nitride residue thereon.
Figure 2:
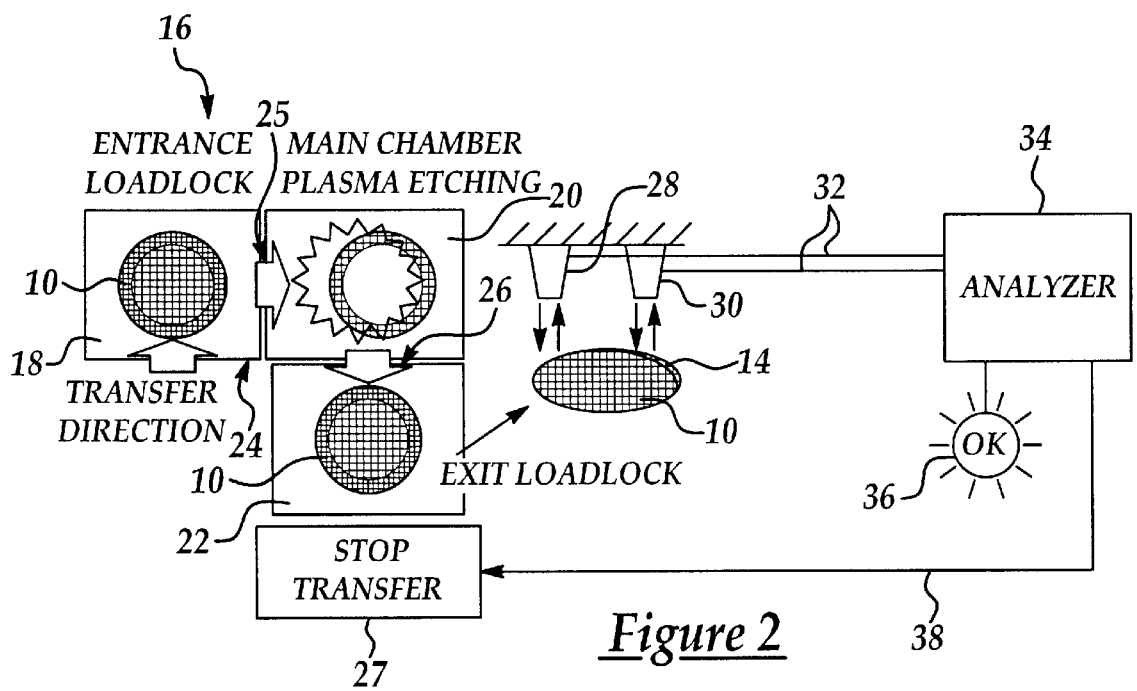
FIG. 2 is a combined diagrammatic and schematic diagram of a system for nitride etching the wafer of FIG. 1A, and incorporating the residue detection apparatus of the present invention.
Figure 3:
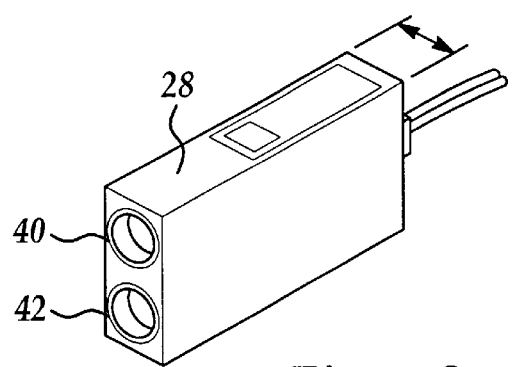
FIG. 3 is a perspective view of one of the color analyzers employed in the system shown in FIG. 2.

Referring now to the drawings, the present invention relates to a method and apparatus for detecting the presence of a nitride residue 14 present on the surface of a semiconductor wafer 10 after a layer 12 of material has been etched away using a conventional nitride plasma etching technique. Although nitride is used as an example in this embodiment, other colored materials such as polysilicon, aluminum or copper can also be used. A typical plasma etching station, generally indicated by the numeral 16 includes an entrance load lock chamber 18, a main chamber 20 in which plasma etching is conducted, and an exit load lock chamber 22 for receiving the wafer 10 after the latter has been etched. An un-etched wafer 10 is initially transported through a load lock door 24 into the entrance load lock chamber 18 where the wafer 10 is retained until it is to be etched. Using conventional, automated transport equipment (not shown), the wafer is transported from chamber 18 through a lock door 25 into the main plasma etching chamber 30 where a conventional plasma etching process is performed employing a nitride to remove a certain amount of film or layer of material present on the surface of the wafer 10. During the course of the etching process, a certain amount of the nitride used in the etching process may remain on the surface of the wafer. Following the etching in the main chamber 20, the wafer is transported through a load lock door 26 into the exit load lock chamber 22 prior to being transported to another processing station where a subsequent process is performed on the wafer 10.

Figure 6:
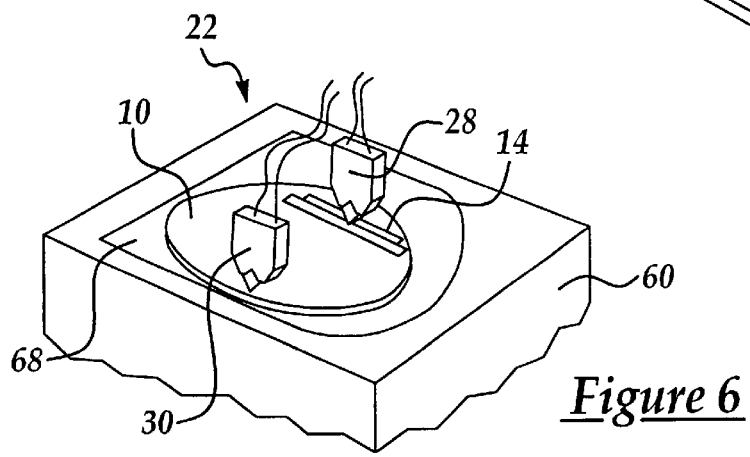

In accordance with the present invention, a system for monitoring and automatically detecting the presence of a nitride residue on the surface of the wafer 10 is provided, which includes a pair of sensors in the form of differential color analyzers 28, 30 which are mounted on appropriate structure (not shown) within the exit load lock 22 so as to view diametrically opposite edges of the wafer 10, as best seen in FIG. 6. Each of the color analyzers 28, 30 is a conventional device, typically including an optical output 40 which directs a beam of visible light onto the surface of the wafer 10, as well as an optical pickup 42 which senses light reflected from the wafer surface that originates from the sensor 28. While any of a number of commercially available color analyzers may be employed as the sensors 28, 30 one suitable sensor may be used which is known as Omron Spectrometer designated by the manufacturers Model # E3C-S7R.

The output of the sensors 28, 30 are respectively connected by lines 32 to a conventional data analyzer 34 which analyzes the outputs of the sensors 28, 30. The outputs of the sensors 28, 30 are signals representative of the magnitude of light reflected from the area of the wafer surface being viewed by the sensor, and having a particular wavelength or range of wavelengths of interest. In the case of nitride residue, the wavelengths reflected by such residue are typically in the range corresponding to the color purple. Consequently the signals delivered on lines 32 to the analyzer 34 are representative of the magnitude of the light received by the corresponding sensor that is within the range of wavelengths that define purple. The analyzer 34 compares these two signal magnitudes with a threshold value. If the comparison is such that the measured light intensity is below the threshold, a signal is issued to activate an annuciator, such as a lamp 36 to indicate that the wafer 10 has passed the inspection test, i.e. there is no nitride residue present on the wafer surface. On the other hand, if the measured intensity of light is above the threshold value, indicating the presence of nitride residue, a signal is issued by the analyzer 34 on line 38 to a mechanism, such as a relay 27 which disables a transport mechanism employed to transport the wafer 10 away from chamber 22 to a subsequent, down-stream processing station. In addition to the threshold comparison described above, the analyzer 34 may operated in a differential mode in which the magnitude of the signals issued by sensors 28, 30, are compared to each other, and/or averaged before the comparison is made with the threshold value.

Figure 4:
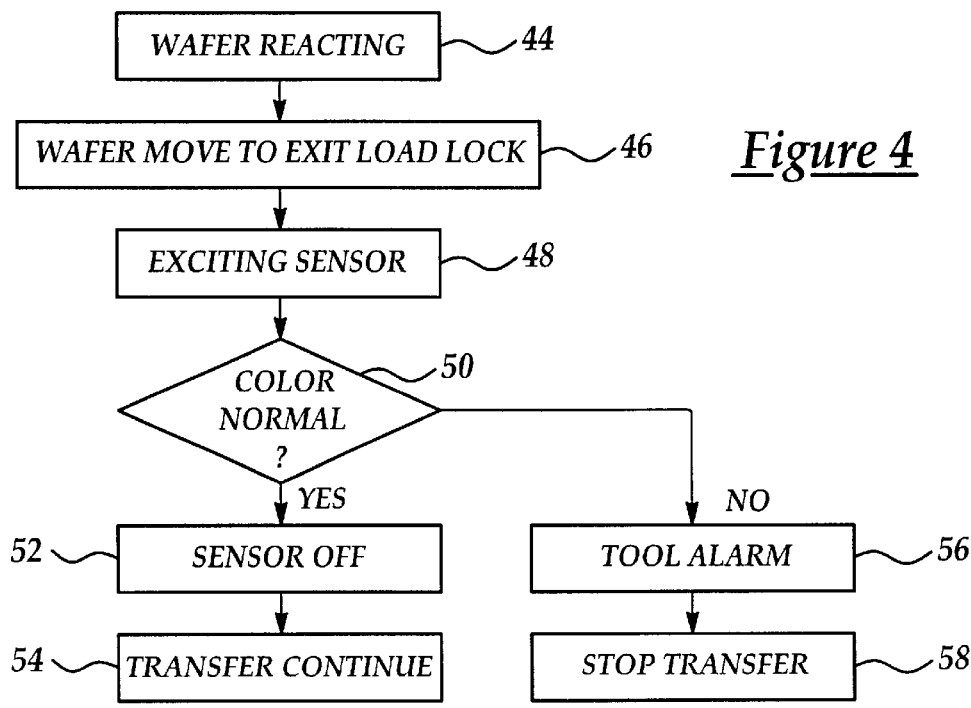
FIG. 4 is a flow chart of the process employed in the system of FIG. 2.
Figure 5:
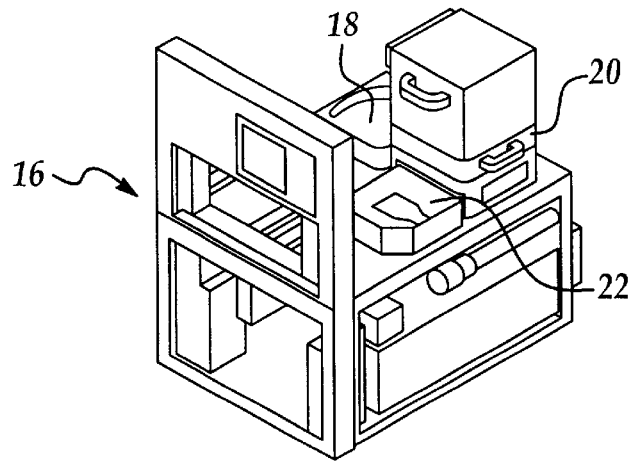
FIG. 5 is a perspective view of a plasma etching station which forms part of the system shown in FIG. 2; and, FIG. 6 is a fragmentary, enlarged view of the exit load-lock chamber forming part of the station shown in FIG. 5.

The inspection and monitoring process described above is shown in the flow chart of FIG. 4. The wafer 10 is first plasma etched in chamber 20 at step 44, following which the wafer 10 is moved through the exit load lock at 46. While the wafer 10 held stationary in the exit load lock 22, the sensors 28,30 are enabled causing them to shine beams of visible light down onto the surface of wafer 10, and the reflectance therefrom is sensed as a signal whose magnitude is proportional to the intensity of the reflected light. The analyzer 34 then determines whether the color of the reflected light is normal, as shown at step 50. If the color is not determined to be normal, an alarm is issued at 56 and subsequent transfer of the wafer 10 is terminated at step 58. On the other hand, if the sensed color is determined to be normal at 50, then the sensors 28, 30 are deactivated at 52, and the wafer 10 is transported to a subsequent processing station at step 54.

The details of the exit load lock 22 and relative mounting of the sensors 28, 30 are better seen in FIG. 6. The wafer 10 lies on a transparent cover 68, such as a sheet of acrylic plastic. The cover 68 in turn rests on an alumina body 60. The sensors 28, 30 are mounted on an appropriate structure (not shown) such that their optical elements are aimed downwardly so as to view diametrically opposite sides of the surface of the wafer 10.

From the foregoing, it is apparent that the method and apparatus described above not only provides for the reliable accomplishment of the objects of the invention but do so in a particularly effective and economical manner. It is recognized, of course, that those skilled in the art may make various modifications or additions to the preferred embodiment chosen to illustrate the invention, without departing from the spirit and scope of the present contribution to the art. Accordingly, it is to be understood that the protection sought and to be afforded hereby should be deemed to extend to the subject matter claimed and all equivalents thereof fairly within the scope of the invention.

What is claimed is:

1. A method and apparatus of detecting the presence of nitride residue on the surface of a semiconductor wafer after said wafer has been etched, comprising the steps of:
   (A) subjecting said wafer surface to light;
   (B) measuring the magnitude of light reflected from said wafer surface having a wavelength within a range of wavelengths characterizing the color of said nitride residue; and,
   (C) comparing the magnitude measured in step (B) with a reference value, the result of the comparison performed in step (C) indicating the presence or absence of said nitride residue on said wafer surface, wherein step A is performed by directing a beam of light generally onto the periphery of said wafer surface, and said directing is performed by delivering first and second beams of light respectively onto generally diametrically opposite sides of said wafer surface.

2. The method of claim 1, wherein said wavelength range is characteristic of the color purple.

3. The method of claim 1, wherein the light to which said wafer surface is subjected includes light within said characterizing wavelengths.

4. A method of etching a layer of material on the surface of a semiconductor wafer, comprising the steps of:
   (A) transporting said wafer into a processing chamber;
   (B) plasma etching said layer on said wafer using an etchant including nitride;
   (C) transferring said wafer out of said chamber when step (B) is completed;
   (D) directing light onto the surface of said wafer after step (C) has been performed; and,
   (E) measuring light reflected from said wafer surface having a wavelength within a range of wavelengths characterizing nitride residue on said wafer surface, wherein steps (D) and (E) are performed by positioning a pair of color analyzers such that said analyzers measure light reflected from diametrically opposite edges of said wafer.

5. The method of claim 4, wherein step (E) is performed using a color analyzer.

6. The method of claim 4, comprising the steps of:
   comparing the magnitude of the light measured in step (E) with a reference value; and,
   issuing an alarm when the measured magnitude of light is greater than said referenced value.

7. The method of claim 4, wherein step D includes exciting a color sensor and said method includes the step of deactivating said color sensor after step E is completed.

8. The method of claim 4, wherein step (C) includes transporting said wafer to an exit load lock station, and steps (D) and (E) are performed while said wafer is present at said exit load lock station.

9. Apparatus for detecting the presence of nitride residue present on the surface of a semiconductor wafer after said wafer has been removed to an exit load lock station from a chamber in which the wafer is etched, comprising:
   a color differential sensor system for differentially sensing and analyzing light reflected from fully etched areas of said wafer surface and from areas containing said residue, the sensed differential indicating the presence or absence of said residue and, first and second color sensors mounted at said exit load lock station and positioned so as to sense the color of light reflected from diametrically opposite sides of said wafer surface.

10. The apparatus of claim 9, including means responsive to said sensor system for controlling the transfer of said wafer.

* * * * *